United States Patent [19]
Anderson

[11] Patent Number: 5,092,466
[45] Date of Patent: Mar. 3, 1992

[54] APPARATUS AND METHOD FOR STORING SAMPLES OF PROTEIN GENE PRODUCTS, INSERT-CONTAINING CELLS OR DNA

[75] Inventor: Norman G. Anderson, Rockville, Md.

[73] Assignee: Large Scale Biology Corportion

[21] Appl. No.: 260,607

[22] Filed: Oct. 21, 1988

[51] Int. Cl.⁵ .................................... B65D 85/50
[52] U.S. Cl. ........................ 206/438; 206/459; 422/66
[58] Field of Search ............ 206/438–441, 206/484, 569, 632, 459; 422/63, 66; 435/1, 2, 243, 287, 299, 260, 284, 300

[56] References Cited

U.S. PATENT DOCUMENTS

| Re. 28,339 | 2/1975 | Maxon | 422/66 |
|---|---|---|---|
| 3,306,894 | 5/1962 | Forestiere | 206/484 |
| 3,726,645 | 4/1973 | Kaczmarek | 206/569 |
| 3,941,661 | 3/1976 | Noteboom . | |
| 3,979,264 | 9/1976 | Buerger | 195/127 |
| 4,363,782 | 12/1982 | Yamashita | 422/66 |
| 4,476,226 | 10/1984 | Hansen et al. | 195/139 |
| 4,504,547 | 3/1985 | Horodniceanu | 435/299 |
| 4,562,159 | 12/1985 | Shafritz | 206/569 |
| 4,565,783 | 1/1986 | Hansen et al. | 428/407 |
| 4,581,874 | 4/1986 | Rechtsteiner et al. | 206/484 |
| 4,637,061 | 1/1987 | Riese | 206/569 |
| 4,657,873 | 4/1987 | Gadow et al. | 435/299 |
| 4,659,672 | 4/1987 | Provonchee et al. | 435/287 |
| 4,714,595 | 12/1987 | Anthony | 206/439 |
| 4,777,964 | 10/1988 | Briggs et al. | 206/569 |
| 4,878,971 | 11/1989 | Tsunekawa et al. | 422/66 |
| 4,881,649 | 11/1989 | Hsu et al. | 206/632 |

FOREIGN PATENT DOCUMENTS

2302247 9/1976 France .................. 206/484

Primary Examiner—Jimmy G. Foster
Attorney, Agent, or Firm—Venable, Baetjer, Howard & Civiletti

[57] ABSTRACT

An apparatus and method for storing samples is disclosed. The samples comprise protein gene products or hybridoma cells, and are sealed in packets which are attached to film. Sample identifiying formation may be printed on the packet and on the film adjacent the packet, and the film is stored wound on reels.

20 Claims, 2 Drawing Sheets

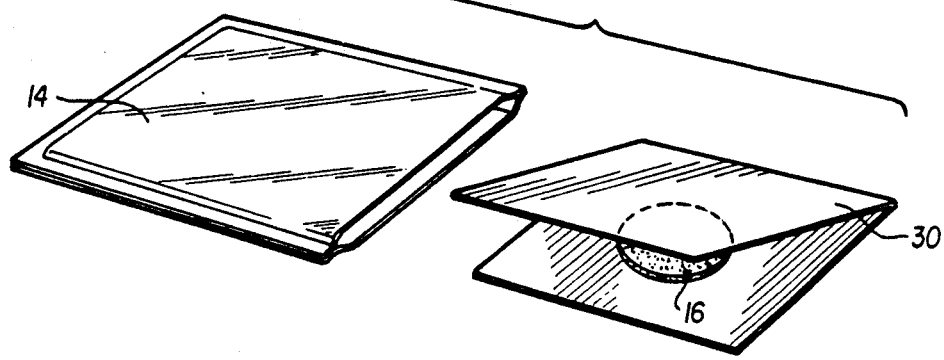
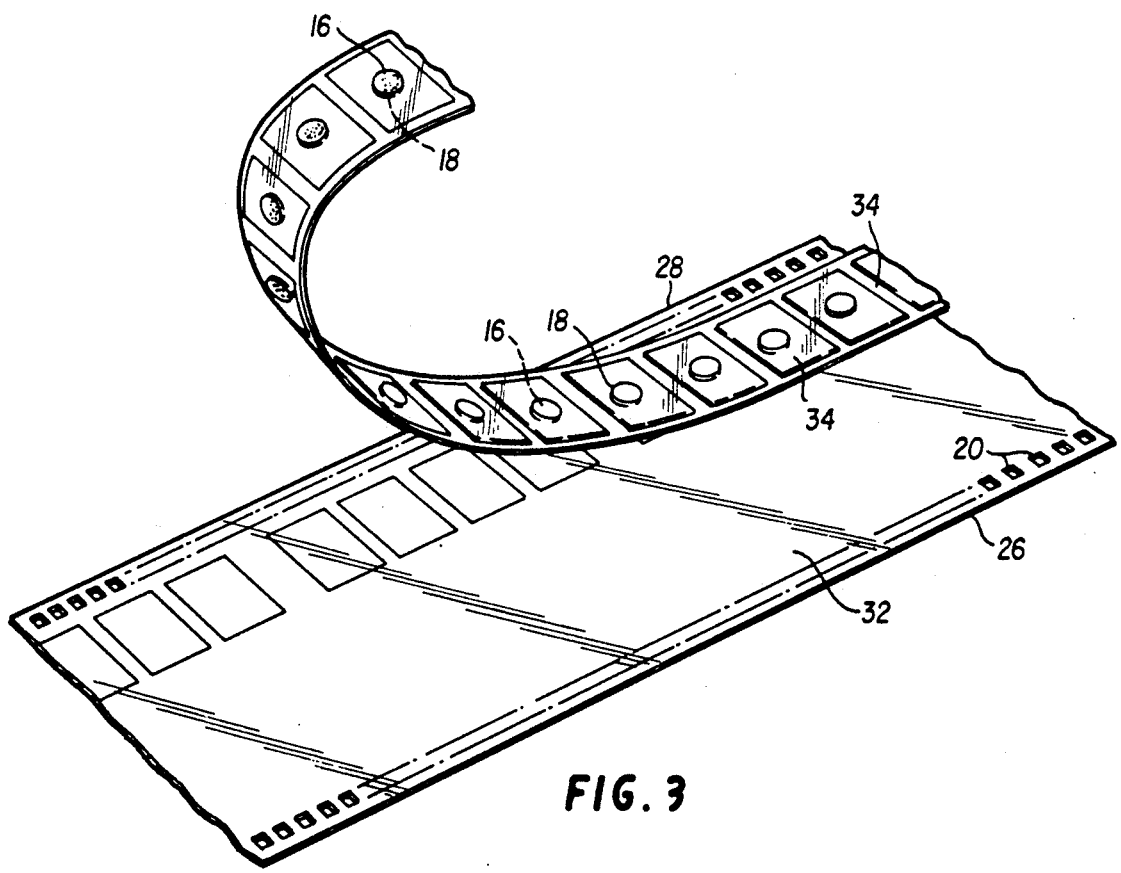

APPARATUS AND METHOD FOR STORING SAMPLES OF PROTEIN GENE PRODUCTS, INSERT-CONTAINING CELLS OR DNA

BACKGROUND OF THE INVENTION

The number of biological samples which will require storage and distribution is expected to increase very rapidly as attempts to map and sequence the human genome and other genomes are made, and as protein gene products are produced together with either polyvalent antibodies or monoclonal antibody producing cells for each protein. To completely sequence the human genome, approximately ten million DNA fragments averaging 300 bases in length are required (using present sequencing methods). These will be produced by restriction enzyme digestion of longer inserts in lambda phage, which in turn will be produced from cosmid inserts (circa 40 kb), which will in turn be produced from yeast artificial chromosomes (approximately 400 kb). More than one genome equivalent of DNA must be considered since overlapping fragments will be required for ordering. All of these samples will need to be preserved for long periods of time, and be readily accessible to researchers.

The estimates of storage, validation and distribution are high, and can reach $1,500 per sample. Estimates of the total number of samples to be stored and distributed will depend on cost since the cost of storing and distributing smaller inserts may be more than the cost of preparing them as needed from larger inserts or artificial chromosomes. Estimated storage, characterization, data management, and distribution costs were estimated at approximately one quarter of a billion dollars ($250,000,000) at the Aug. 6, 1987 meeting on "The Cost of Human Genome Projects" sponsored by The Office of Technology Assessment of the U.S. Congress. Estimates of the total number of samples needed to be stored for the human genome sequencing project alone run as high as ten million.

Using conventional storage methods, many useful samples may not be stored because re-isolation may be cheaper than storage with present methods and equipment. If storage and distribution costs can be markedly reduced, the burden of re-isolated fragments previously isolated may be reduced. The larger the number of samples that can be efficiently stored and retrieved, the less the amount of effort required for individual investigators.

Since the purpose of any genome sequencing project is to provide both experimental material and data (the sequence and the gene) to individual investigators, it is important to provide as complete a library of samples as possible at the lowest possible cost. Present technology as developed over a period of approximately thirty years at the American Type Culture Collection includes the storage of cells at liquid nitrogen temperatures ($-196°$ C.) and the storage of lyophilized cells at higher temperatures, often at $-70°$ C. ($-94°$ F.). Storage has traditionally been in heat-sealed glass vials. There are the attendant problems of keeping labels attached, of including as large an amount of data on the labels as possible, of maintaining records of sample location (in a large farm of liquid nitrogen tanks and mechanical refrigerators) and of sample origin, classification, and descriptive text, and keeping records of distribution and use experience.

SUMMARY OF THE INVENTION

The invention relates to a method for storing samples in which the samples are preserved in hermetically sealed packets and the packets are mounted on film. The invention also relates to an apparatus for storing samples comprising a film and hermetically sealed packets containing preserved samples mounted thereon.

The samples comprise protein gene products, cells, or DNA and are generally preserved by freezing or lyophilization. Identifying material may be printed on the sample packetting material and/or the film, and the films are stored in a rolled form on reels. The reels may be scanned electronically for inventory checking, and segments of film at predetermined positions removed for distribution.

It is expected that the present invention will markedly reduce the costs of storage, inventory management, and distribution of the very large numbers of biological samples that will be generated by genome mapping and sequencing projects, by widespread hybridoma utilization, and by the growth of the biotechnology field.

BRIEF DESCRIPTION OF THE DRAWINGS

The various objects, advantages and novel features of the invention will be more readily appreciated from the following detailed description when read in conjunction with the appended drawings in which:

FIG. 2 is a perspective view of one embodiment of a packet used in the apparatus shown in FIG. 1; and FIG. 3 is a perspective view of an alternative embodiment of the present invention.

DETAILED DESCRIPTION OF THE INVENTION

Figure 1:
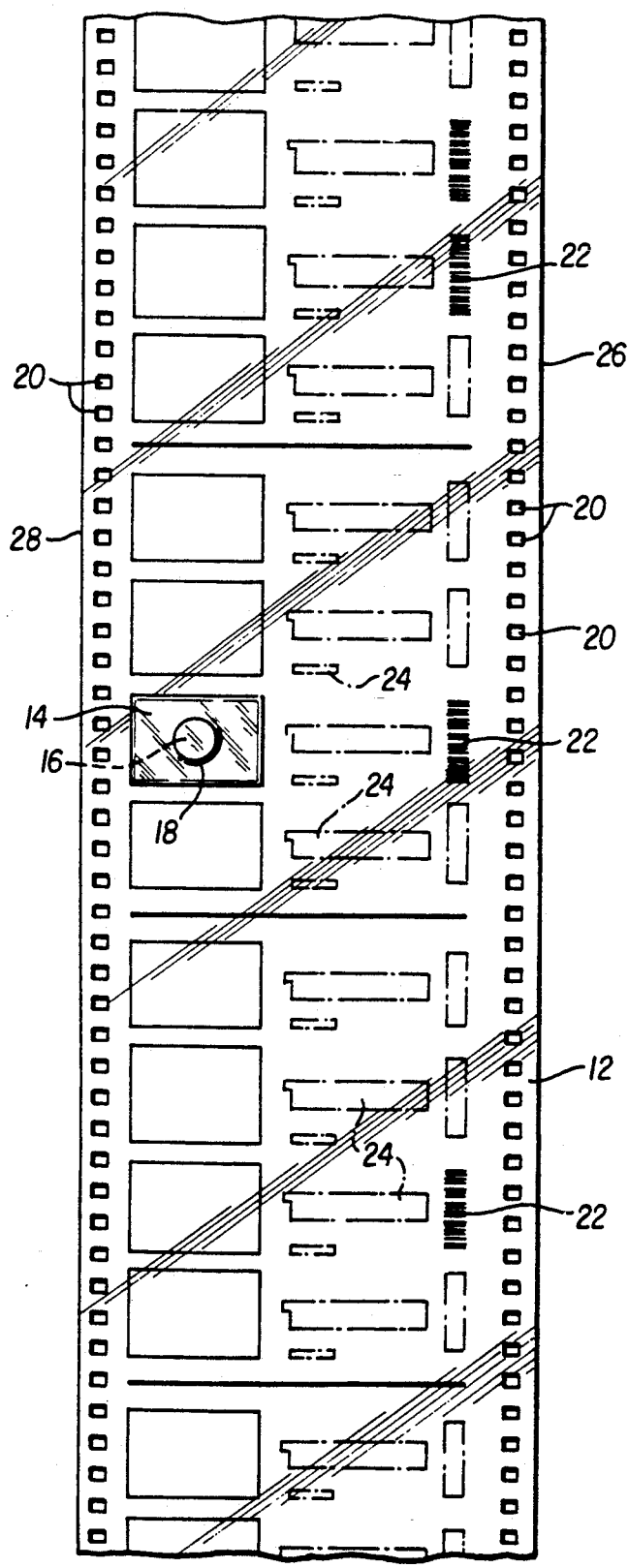
FIG. 1 is a perspective view of the apparatus for storing samples constructed in accordance with the present invention.

The term "sample" is used to describe protein gene products, hybridoma cells, yeast cells containing artificial chromosomes, E. coli containing cosmids or lambda phage or other vectors, cosmids, lambda phage or other vectors themselves, and purified DNA or RNA.

FIG. 1 illustrates the apparatus and method used to store samples. A film 12 has mounted thereon sealed packets 14 containing samples 16.

The film provides a convenient and efficient method of storing samples 16. The film 12 is easily rolled onto reels much like motion picture film, and therefore takes up much less space than conventional storage methods.

The samples 16 can be easily and exactly located on the film by counting sprocket holes 20 and/or scanning for bar codes 22 or other machine readable identification. When using the counted sprocket hole method of location, a system of recording the sprocket hole location of each sample when it is attached to the film is used. Type II standard motion picture sprocket holes 22 are preferred for the film 12.

Adjacent each sample containing packet 14 on the film 12, is preferably alphanumeric data 24. The alphanumeric data 24 may identify the sample, provide a history of the sample and its preparation, list the composition of the sample or provide any other desired information.

The samples 16 are retrieved from the film 12 by cutting or punching out the desired sample containing packet 14 and its corresponding alphanumeric data 24.

From its stored position rolled on a reel, the film 12 is unwound and the location of the desired sample is determined by sprocket hole counting or scanning of machine readable information such as the bar codes 22. After the desired sample 16 is located, the section of the film 12 on which the desired packet 14 and corresponding alpha-numeric data 24 is located is removed by cutting or other suitable method. The removal method should leave film 12 capable of being rewound onto a reel. There should not be a direct severance of film 12 from one lengthwise edge 26 to the other lengthwise edge 28. The film 12 is rewound onto a reel and restored after removal of the desired samples 16.

The samples 16 may include protein gene products, hybridoma cells, yeast cells containing artificial chromosomes of human DNA, and *E. coli* containing cosmid and lambda phage, cosmids and lambda phage themselves, or purified samples of DNA.

Before the samples 16 are sealed in the packets 14, the samples are preferably absorbed into a porous material 18 and preserved. Absorption of the sample 16 into the porous material 18 serves to retain the sample in a configuration which optimizes preservation of the sample.

A preferred porous material is filter paper. However, other suitable materials include cotton, gauze, cellulose, clay, and other types of paper.

Preferred forms of preservation of the samples 16 are freezing and lyophilization (often referred to as freeze-drying). Lyophilization is a process of drying in which water is sublimed from the product after the product is frozen.

A general conventional lyophilization process involves the following steps:
1. Freezing an aqueous product at a temperature below its eutectic temperature;
2. Evacuating the chamber, usually below 0.1 Torr (100 mcm Hg);
3. Subliming ice on a cold condensing surface at a temperature below that of the product, the condensing surface being within the chamber or in a connecting chamber; and
4. Introducing heat to the product under controlled conditions, thereby providing energy for sublimation at a rate designed to keep the product temperature below its eutectic temperature.

Most commonly, the product is frozen by circulating a refrigerant such as Freon, ammonia or ethylene glycol, and evacuation of the chamber is conducted with a vacuum pump. Heat for sublimation of the ice is commonly provided by electric resistance coils or by circulating hot water or hot glycol.

Preferably, the samples 16 are preserved before being sealed in the metallized plastic packet 14. The packets are preferably sealed ultrasonically, and identifying bar coding or text may be ink jet printed on the sealed envelope. The packets should be capable of hermetic sealing, have exterior surfaces which are sterilizable, be flat and occupy a minimum volume, and be attachable to the film 12.

The packet 14 is preferably rectangular in shape with a length dimension of about 1–3 cm and a width dimension of about 1–3 cm. The packet 14 must have dimensions which allow it to fit on the film 12 and leave room for the alphanumeric data 24 adjacent thereto. The packet 14 must also have sufficient volume to contain the porous material 18 and sample 16. A preferred volume of the packet 14 is about 0.1 ml.

When the sample 16 is to be stored as a frozen liquid, the sample is aliquoted into the packet 14 under sterile conditions. The packet 14 is then sealed with a specially designed sonicator which applies pressure evenly along the packet edges, but does not heat the center of the packet 14 where the porous material 18 and the sample 16 are located. The packet 14 is then sterilized in any suitable manner such as placing the sealed packet 14 in a solution of diethylcarbamate.

Alternatively, the sample 16 may be preserved by lyophilization. In a preferred method of lyophilization, unsealed packets 14 containing the samples 16 are attached to a specially designed rack, frozen, and placed in a container which is attached through a heated metal loop to a standard lyophilizer. The heated loop incinerates any particles passing in either direction. Valving allows the evacuated container with dried samples to be removed from the system, and a unique metal bellows system allows the packets 14 to be sealed ultrasonically while in vacuum. After removal from the evacuation chamber, the packets are resealed as a precaution and sterilized before attachment to the film 12. The evacuation chamber and all attachments, including the heated loop are sterilized before reuse. Methods of sealing metallized plastic envelopes while maintaining sterility are well known in the pharmaceutical arts.

After preservation of the sample 16, the packet 14 is sealed as described above. It is very important that the packet 14 be essentially leak-proof after sealing so as to avoid cross-contamination of the samples or damage to the samples from atmospheric exposure.

As shown in FIG. 2, the inclusion of a very small flat expanding spring-like device 30 serves to indicate gross leakage over time, since the packet loses its compressed appearance and begins to expand. An alternative method for determining leakage involves bleeding helium into the lyophilization chamber after it has been closed off from the main vacuum chamber and the intervening high temperature connection. If there are microleaks in the packets 14, helium will very slowly leak in. If the surrounding helium is then flushed out with air, and the chamber then quickly partially reevacuated, helium leakage from the packets may be then detected using a helium leak detector. This technique, or some modification of it, may serve as a final check of the efficiency of sealing.

After the sample 16 has been preserved and the packet 14 has been sealed and sterilized, the sample containing packet is ready to be attached to the film 12. Attachment of the sealed packet 14 to the film 12 may be accomplished in any suitable manner such as by use of a flexible cement which does not become brittle at low temperature. Alternative methods of attachment include the use of metal or plastic rivets or the use of ultrasonic melting of plastic of the packets with or without flow through very small holes in the film 12. Ultrasonic heating of plastics is a highly localized technique, and with the use of suitable heat sinks, only a small highly defined area is heated.

The film 12 with the packetted samples attached is stored in a wound form on standard or adapted reels used for 100 foot or 1000 foot rolls of film. Storage of the reels of film must be in a moisture-free environment so that frost does not occur. Storage depends on the type of sample and may be at +5° C. for lyophilized samples, −16° C., −20° C., −70° C. or in liquid nitrogen storage chambers for cells, in which case all reel handling must be done remotely.

Recovery of the samples 16 from the film 12 is performed by attaching an end of the film 12 to a second reel and unwinding the film 12 from the first reel onto the second reel. As the film 12 is unwound, it is passed under a scanner which locates the desired sample by sprocket hole counting or reading a machine readable code. The desired sample and its corresponding alphanumeric data is then positioned and punched out of the film 12, leaving the perforated edges of the film intact.

Segments of film with attached samples may also be cut out with perforations, and the free film ends ultrasonically welded together using ultrasonic film splicers well known in the motion picture industry.

An advantage of complete excision of a film segment is that the film strip is shortened by the length removal, hence the method is a so-called "push down" storage method in which removal of samples increases the storage space available.

An additional advantage of complete excision is that the excised segments may be spliced together ultrasonically giving the user a collection of samples which may be arranged in the order preferred by the user.

The packaging of the samples 16 is designed for users of several levels of sophistication. The samples 16 may be sealed in a somewhat larger metallized plastic packet and sent in a letter or shipped in an insulated container if the sample 16 must remain frozen.

To use the sample, the user first sterilizes the exterior of the packet by any suitable method such as placing it in a solution of diethylcarbamate. The packet is then submerged in a vial containing a reconstitution liquid such as 0.9% sodium chloride. When completely submerged, a sterile pointed scalpel is used to puncture the packet. If the packet contains lyophilized material or a porous support, the reconstitution liquid will be drawn into the packet and reconstitute the sample. After two to five minutes, the sample should be completely reconstituted and the packet may be cut open under the liquid and part of the contents squeezed out.

In a preferred embodiment shown in FIG. 2, a spring-like device 30 may be included in the packet 14. The packet remains in a compact state by external air pressure until the packet is punctured at which time the spring-like device 30 causes the packet 14 to expand. The spring-like device 30 also serves as a leakage alert system during storage and shipping of packet 14.

The sample-containing packets 14 which are shipped frozen may be similarly sterilized externally and cut open under liquid after thawing. Alternatively, if sample dilution is to be avoided, the packet may be punctured, placed in a sterile centrifuge with a cap that holds the packet, and the contents of the packet centrifuged out.

A further alternative method of shipping and using the packetted samples is to ship the packet in a sterile condition in a second larger packet. Under such conditions, the user may choose to sterilize the external packet, open it under sterile conditions, and then remove the contents of the internal packet in any of a variety of ways. For example, if freeze-dried cells are dried on a square of filter paper, the paper with attached cells may be cut up, and small pieces placed in separate tubes. Or only part of the paper may be removed, and the packet resealed and stored at a low temperature.

When alphanumeric data or machine readable information is printed on the packets as well as the film, the film may be scanned to insure that the packet and film data conform with one another for inventory purposes. This type of inventory scanning will also identify those portions of the film from which sample containing packets have been removed. An advantage of this storage system is that packets which become detached from the film may be discovered during the inventory scanning procedure.

An alternative embodiment of the invention, shown in FIG. 3 comprises a sandwich-type arrangement of two the films 32 and 34 with the samples 16 therebetween. The samples 16 are preferably absorbed into a porous material 18 which is placed on film 32. The covering film 34 is placed over the film 32 with the samples 16 and the porous material 18 sandwiched between the two films. A specialized sonicator is then used to ultrasonically fuse the covering film 34 and the film 32 to one another in such a manner as to create a packet-like enclosure 36 surrounding the samples 16 and the porous material 18.

This packet-like enclosure 36 has dimensions which approximate those of the packet 14 described above. The length of the packet-like enclosure 36 is about 1-3 cm and its width is about 1-3 cm, while the volume enclosed is about 0.01 ml to about 0.2 ml and preferably about 0.1 ml. The length and width dimensions of the packet-like enclosure 36 define the boundary of the unfused areas of film.

Bar codes 22 and/or alphanumeric data 24 may be printed on either film 32 or covering film 34 and both films preferably have sprocket holes 20 located along their lengthwise edges 26 and 28. The removal and recovery of the samples 16 from the alternative embodiment storage system is identical to the removal procedures described above when packetted samples 16 are attached to the film 12.

With present biological storage systems, it is extremely difficult to physically check inventory for errors, or in cases where electronically stored, data is lost. With the system described here, inventory can be checked by scanning the reels with a bar code reader, thus greatly reducing errors and inventory checking costs.

Samples can be categorized into at least three classes, which include (a) those of sufficient interest to be stored but which are very infrequently distributed, (b) samples distributed with sufficient frequency to maintain them on an active list (there may be several subgroups of this classification), and (c) sets of samples which will be desired as a set by many different laboratories (for example, genes for all mitochondrial proteins of human liver). It is therefore important to be able to remove samples with identifying text from one film strip and attach it to another. With the use of very small plastic rivets or ultrasonic welding, this is possible. Therefore, large laboratories desiring, for example, an ordered set of yeast cells containing artificial chromosomes covering one human genome, may be able to obtain it, all ordered, on a set of film reels. For very popular samples, whole reels may be prepared containing one or only a few species of samples.

While the invention has been disclosed by reference to the details of various embodiments of the invention, it is understood that this disclosure is intended in an illustrative rather than in a limiting sense, as it is contemplated that modifications will occur to those skilled in the art, within the spirit of the invention and the scope of the appended claims.

What is claimed is:

1. A method for storing a sample comprising the steps of:
   (a) preserving the sample;
   (b) enveloping the sample in a hermetically sealed packet;
   (c) mounting the packetted sample on film; and
   (d) removing the packetted sample from the film by punching out a portion of the film on which the packetted sample is mounted without completely severing the film.

2. The method of claim 1 wherein the preservation of the sample comprises freezing or lyophilizing the sample.

3. The method of claim 1 wherein the hermetically sealed packet comprises a metallized plastic.

4. The method of claim 3 further comprising the inclusion of a porous material within the hermetically sealed packet.

5. The method of claim 4 wherein the hermetic sealing is performed by applying pressure or heat to edges of the packet with substantially no pressure or heat applied to the center of the packet.

6. The method of claim 1 wherein identifying material is printed on the packet.

7. A method for storing a sample comprising the steps of:
   (a) preserving the sample;
   (b) enveloping the sample in a hermetically sealed packet;
   (c) mounting the packetted sample on film; and
   (d) removing the packetted sample from the film by cutting out a portion of the film on which the packetted sample is mounted and completely severing the film.

8. The method of claim 7 further comprising splicing the two severed ends of the film.

9. A method for storing samples comprising:
   (a) preservation of the samples;
   (b) sandwiching of the samples between two films;
   (c) fusing of the films to create packet-like enclosures surrounding said samples; and
   (d) removing a packetted sample from the film by punching out a portion of the film on which the packetted sample is mounted without completely severing the film.

10. The method of claim 9 wherein preservation of the samples comprises freezing or lyophilizing the samples.

11. The method of claim 9 further comprising the inclusion of a porous material within the packet-like enclosure.

12. The method of claim 9 wherein identifying material is printed on at least one of the two films.

13. A method for storing samples comprising:
    (a) preservation of the samples;
    (b) sandwiching of the samples between two films;
    (c) fusing of the films to create packet-like enclosures surrounding said samples; and
    (d) removing a packetted sample from the film by cutting out a portion of the film on which the packetted sample is mounted and completely severing the film.

14. The method of claim 13 further comprising splicing the two severed ends of the film.

15. An apparatus for storing samples comprising:
    (a) a film;
    (b) at least one hermetically sealed packet containing a preserved sample mounted on said film; and
    (c) identifying material printed on the film.

16. The apparatus of claim 15 wherein the preserved sample is a frozen or lyophilized sample.

17. The apparatus of claim 15 further comprising a porous material within the packet.

18. The apparatus of claim 15 wherein identifying material is printed on the hermetically sealed packet.

19. An apparatus for storing samples comprising:
    (a) a porous film; and
    (b) at least one hermetically sealed packet containing a preserved sample mounted on said film.

20. The apparatus of claim 19 wherein identifying material is printed on the film.

* * * * *